United States Patent [19]

Liu

[11] Patent Number: 4,568,382
[45] Date of Patent: Feb. 4, 1986

[54] HERBICIDAL COMPOUNDS, COMPOSITIONS, AND METHOD OF USE

[75] Inventor: Kou-Chang Liu, Wayne, N.J.

[73] Assignee: GAF Corporation, Wayne, N.J.

[21] Appl. No.: 557,570

[22] Filed: Dec. 2, 1983

Related U.S. Application Data

[63] Continuation-in-part of Ser. No. 283,402, Jul. 15, 1981, Pat. No. 4,435,588.

[51] Int. Cl.$^4$ .................. A01N 37/44; C07C 79/46
[52] U.S. Cl. ........................... 71/111; 71/108; 560/21
[58] Field of Search ............... 560/21; 71/111, 108

[56] References Cited

U.S. PATENT DOCUMENTS 3,282,991 11/1966 Klein et al. .................. 560/103

FOREIGN PATENT DOCUMENTS 0020052 12/1980 European Pat. Off. .......... 560/21

Primary Examiner—Paul J. Killos
Attorney, Agent, or Firm—Marilyn J. Maue; Joshua J. Ward

[57] ABSTRACT

Novel and highly effective herbicidal compounds in the diphenylether class are provided herein.

1 Claim, No Drawings

HERBICIDAL COMPOUNDS, COMPOSITIONS, AND METHOD OF USE

This is a continuation-in-part application of Ser. No. 283,402, filed July 15, 1981 and entitled "Herbicidal Compounds, Compositions, And Method Of Use", U.S. Pat. No. 4,435,588.

BACKGROUND OF THE INVENTION

1. Field of the Invention

This invention relates to novel compounds which are active herbicides.

2. Description of the Prior Art

Certain phenoxybenzoates show herbicidal activity and are disclosed in e.g. U.S. Pat. Nos. 3,652,645; 3,784,635; 3,798,276; 3,928,416; 3,941,830; 3,979,437; 4,001,005; 4,002,662; 4,046,798; 4,063,929; 4,164,408; 4,164,409; 4,164,410; 4,178,169 and 4,185,995. However, the herbicidal effectiveness and selectivity of a given phenoxybenzoate cannot be predicted from an examination of its chemical structure. Often quite closely related compounds will have quite different weed control abilities and crop selectivity.

SUMMARY OF THE INVENTION

In accordance with the present invention, there is provided novel herbicidal phenoxybenzoates having the formula:

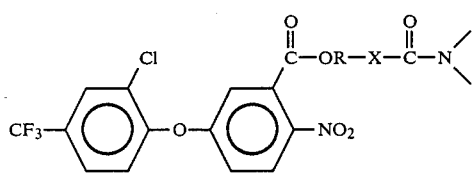

R is a saturated or olefinically unsaturated hydrocarbon radical of 1 to 6 carbon atoms which may contain oxygen, as in the radical —R—O—R—; X is S, O or NH; $R_1$ is $C_{1-6}$ alkyl or $C_{2-6}$ alkenyl and $R_2$ can be methyl when X is oxygen and can be $C_{2-6}$ alkyl or $C_{2-6}$ alkenyl when X is S, O or NH. The preferred alkyl and alkenyl groups are those having from 1 to 3 carbon atoms and most preferred are those compounds wherein $R_1$ and $R_2$ are the same.

The novel compounds of the invention have been found to show excellent activity as weed control agents and high selectivity towards major agricultural crops including rice, soybean and corn.

Non-limiting examples of the compounds of this invention embraced within the formula scope of this invention are set forth in Table I.

TABLE I

| Ex. No. | Compound | X | R | $R_1$ | $R_2$ |
|---|---|---|---|---|---|
| 1 | 2-(N,N—Diethylcarbamyloxy)ethyl 5-(2-chloro-4-trifluoromethyl-phenoxy)-2-nitrobenzoate | O | —CH$_2$CH$_2$— | —CH$_2$CH$_3$ | —CH$_2$CH$_3$ |
| 2 | 2-(N,N—Dimethylcarbamyloxy)ethyl 5-(2-chloro-4-trifluoromethylphenoxy)-2-nitrobenzoate | O | —CH$_2$CH$_2$— | —CH$_3$ | —CH$_3$ |
| 3 | 6-(N,N—Dimethylcarbamyloxy)hexyl 5-(2-chloro-4-trifluoromethylphenoxy)-2-nitrobenzoate | O | —(CH$_2$)$_6$— | —CH$_3$ | —CH$_3$ |
| 4 | 5-(N,N—Dimethylcarbamyloxy)-3-oxapentyl 5-(2-chloro-4-trifluoromethylphenoxy)-2-nitrobenzoate | O | —C$_2$H$_4$OC$_2$H$_4$— | —CH$_3$ | —CH$_3$ |
| 5 | 2-(N,N—Dimethylcarbamyloxy) 2 buten-1-yl 5-(2-chloro-4-trifluoromethylphenoxy)-2-nitrobenzoate | O | —CH$_2$CH=CHCH$_2$— | —CH$_3$ | —CH$_3$ |
| 6 | 2-[(N,N—Diethylcarbamyl)-amino]ethyl 5-(2-chloro-4-trifluoromethylphenoxy)-2-nitrobenzoate | NH | —CH$_2$CH$_2$— | —CH$_2$CH$_3$ | —CH$_2$CH$_3$ |
| 7 | 2-[(N,N—Diallylcarbamyl)amino]ethyl 5-(2-chloro-4-trifluoromethylphenoxy)-2-nitrobenzoate | NH | —CH$_2$CH$_2$— | —CH$_2$CH=CH$_2$ | —CH$_2$CH=CH$_2$ |

DETAILED DESCRIPTION OF THE INVENTION

The compounds (V) of the invention are made by reacting precurser (I) with (II); or precurser (III) with (IV), as follows:

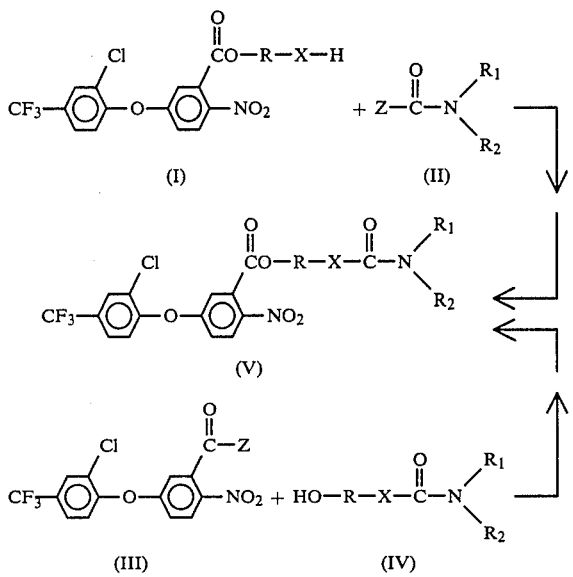

where Z is chlorine or bromine and R, $R_1$, X and $R_2$ are as defined above. The reactions may be carried out in the presence or absence of a base, and with or without a solvent.

Compound (I) is prepared by reacting the corresponding 2-chloro-4-trifluoromethyl-phenoxybenzoic acid halide with a glycol reactant; whereas Compound (IV) is synthesized by reacting

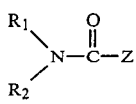

with a glycol reactant. All of the above reactions are carried out at a temperature between about 40° C. and about 120° C. under atmospheric pressure in the presence or absence of a base, and with or without a solvent. Suitable solvents include methylene chloride, tetrahydrofuran, p-dioxane and the like. The base, when employed, includes such compounds as triethylamine, pyridine, potassium carbonate and the like.

Compound I may also be prepared from the corresponding alcohols by their reaction with the corresponding 4-trifluoromethyl-2-chloro-phenoxybenzoic acid in the presence of an acid catalyst.

The compounds of this invention are useful both as pre-emergent and post-emergent herbicides. Among the crops on which the compounds may be advantageously employed are, for example, soybean, rice, corn, cotton, wheat, sorghum, peanuts, safflower, beans, peas, carrots, and other cereal crops.

The phenoxybenzoates of this invention may be applied in any amount which will give the required control of weeds. A preferred rate of application of these benzoates is from 0.05 to 8 lbs. per acre. In practical application, the compounds may be applied in solid, liquid or in vaporized form, and generally as an active ingredient in a herbicidal composition or formulation which comprises the herbicide and a carrier. Suitable carriers are substances which can be used to dissolve, disperse or diffuse the herbicidal components in the composition. Non-limiting examples of liquid carriers include water, organic solvents such as alcohols, ketones, halogenated hydrocarbons, aromatic hydrocarbons, ethers, amides, esters, nitriles, mineral oils and the like. Non-limiting examples of solid carriers include Kaolin, bentonite, talc, diatomaceous earth, vermiculite, clay, gypsum, grain and seed hulls, ground corn cobs and the like. In addition to a carrier, it may be desirable to add to the composition additives such as emulsifying agents, wetting agents, binding agents, stabilizer and the like. The compounds can be formulated, for example, as a dust, wettable powder, emulsifiable concentrate, granular formulation or aerosol.

Having thus generally described the invention, reference is now had to the following examples which serve to illustrate preferred embodiments of the invention but which are not to be construed as limiting to the scope thereof as more broadly defined above and in the appended claims.

EXAMPLE 1

Preparation of 2-(N,N-Diethylcarbamyloxy)ethyl 5-(2-chloro-4-trifluoromethylphenoxy-2-nitrobenzoate (A)
5-(2-chloro-4-trifluoromethylphenoxy)-2-nitrobenzoyl chloride.

A solution of 5-(2-chloro-4-trifluoromethylphenoxy)-2-nitrobenzoic acid (448.1 g, 1.24 mole), thionyl chloride (458 g) and toluene (250 ml) was held at reflux for 8 hrs. The excess thionyl chloride and the solvent were stripped off under reduced pressure to give a reddish solid, which upon recrystallization from hexane-toluene afforded 282.9 g of the desired benzoyl chloride as a light yellow crystalline solid; mp 63°-69° C.

(B) 2-Hydroxyethyl 5-(2-chloro-4-trifluoromethylphenoxy)-2-nitrobenzoate.

A well-stirred solution of 5-(2-chloro-4-trifluoromethylphenoxy)benzoyl chloride (282.9 g, 0.74 mole) and ethylene glycol (1000 ml) was heated at 145° C. for 3 hours. Then triethylamine (30 ml) was added. The solution was reheated at 142° C. for 8 hours. After most of the ethylene glycol was distilled off under reduced pressure, the oil was taken up in 1700 ml of methylene chloride. The methylene chloride solution was washed three times with water, dried over MgSO4 and concentrated to a gummy material. Molecular distillation afforded 226.2 g (75% yield) of a pale yellow gum which solidified on standing. 3.5 g of the solid was recrystallized from hexane-toluene to give 2.8 g of white solid; mp 75°-78° C.; nmr (CDCl$_3$) δ0.3.32 (S, 1H), 3.67–4.12 (m, 2H), 4.15–4.63 (m, 2H), 7.02–8.25 (m, 6H); ir (CHCl$_3$) 1749 Cm$^{-1}$.

(C) 2-Hydroxyethyl 5-(2-chloro-4-trifluoromethylphenoxy)-2-nitrobenzoate (6 g, 0.015 mole) and diethylcarbamyl chloride (2 g, 0.015 mole) were heated in an oil bath at 100° C. for 5 hrs., cooled and taken into 300 ml of ether. The ethereal solution was washed three times, dried over CaSO$_4$ and concentrated to a yellow oil. The oil was column chromatographed through silica gel with 20% ethyl acetate-80% hexane as eluent to give 2.2 g pure 2-hydroxyethyl 5-(2-chloro-4-trifluoromethylphenoxy)-2-nitrobenzoate as a gum; nmr (CDCl$_3$) δ110 ir (CHCl$_3$) 1720, 1760 Cm$^{-1}$.

EXAMPLES 2 THROUGH 5

The following compounds were prepared using procedures similar to that described in Example 1.

(2) 2-(N,N-Dimethylcarbamyloxy)ethyl 5-(2-chloro-4-trifluoromethylphenoxy)-2-nitrobenzoate; nmr δ(DMSO-d$_6$) 2.86 (s, 6H), 4.20–4.76 (m, 4H), 7.22–8.29 (m, 6H); ir (CHCl$_3$) 1702, 1748 cm$^{-1}$.

(3) 6-(N,N-Dimethylcarbamyloxy)hexyl 5-(2-chloro-4-trifluoromethylphenoxy)-2-nitrobenzoate; nmr (CDCl$_3$) δ1.06–2.08 (m, 8H), 2.90 (s, 6H), 4.09 (t, 2H), 4.30 (t, 2H), 6.98–8.21 (m, 6H); ir (CHCl$_3$) 1696, 1742 cm$^{-1}$.

(4) 5-(N,N-Dimethylcarbamyloxy)-3-oxapentyl 5-(2-chloro-4-trifluoromethylphenoxy)-2-nitrobenzoate; nmr (CDCl$_3$) δ2.92 (s, 6H), 3.72 (m, 4H), 4.20 (m, 2H), 4.50 (m, 2H), 7.00–8.26 (m, 6H); ir (CHCl$_3$) 1700, 1746 Cm$^{-1}$.

(5) 4-(N,N-Dimethylcarbamyloxy-2-buten-1-yl 5-(2-chloro-4-trifluoromethylphenoxy)-2-nitrobenzoate; nmr (CDCl$_3$) δ2.92 (s, 6H), 4.72 (m, 2H), 4.98 (m, 2H), 5.86 (m, 4H), 7.00–8.22 (m, 6H); ir (CHCl$_3$) 1750, 1710, 1594 Cm$^{-1}$.

EXAMPLE 6

Preparation of 2-[(N,N-Diethylcarbamyl)amino]ethyl 5-(2-chloro-4-trifluoromethylphenoxy)-2-nitrobenzoate (A) N,N-Diethyl-N'-hydroxyethyl urea.

N,N-Diethylcarbamyl chloride (8.2 g, 0.06 mole) in THF (15 ml) was added dropwise to a solution of aminoethanol (3.08 g, 0.05 mole), triethylamine (6.08 g, 0.06 mole) and THF (25 ml) at 0° C. The mixture was stirred at room temperature for 60 hrs., filtered and concentrated to 9.0 g of N,N-diethyl-N'-hydroxyethyl urea as a pale yellow oil; nmr (CDCl$_3$) δ1.15 (t, 3H), 2.88–3.84 (m, 8H), 5.26 (s, broad, 1H), ir (neat) 3380, 1620 Cm$^{-1}$.

(B) 5-(2-chloro-4-trifluoromethylphenoxy)-2-nitrobenzoyl chloride (3.8 g, 0.010 mole) in 15 ml of THF was added dropwise to a solution of N,N-diethyl-N'-hydroxyethyl urea (2.5 g, 0.015 mole), triethylamine (1.2 g, 0.012 mole) and THF (25 ml) at 0° C. The resulting mixture was stirred at room temperature overnight, filtered and concentrated. The residue was taken into 75 ml of methylene chloride, washed three times with a saturated NaHCO$_3$ solution and one time with water. After being dried over Na$_2$SO$_4$ and concentrated, a brown oil (5.0 g) was afforded. The oil was column chromatographed through silica gel with 50% ethyl acetate-50% cyclohexane as eluent to give 3.3 g of 2-[(N,N-diethylcarbamyl)amino]ethyl 5-(2-chloro-4-trifluoromethylphenoxy)-2-nitrobenzoate as a brown solid; mp 89°–90° C.; nmr (CDCl$_3$) δ1.12 (t, 6H), 3.23 (q, 4H), 3.67 (t, 2H), 4.46 (t, 2H), 4.95 (s, broad 1H), 6.92–8.28 (m, 6H); ir (CHCl$_3$) 3485, 1750, 1680 Cm$^{-1}$.

EXAMPLE 7

Compound 7 was prepared using the procedure of Example 6. The product 2-[(N,N-diallylcarbamyl)amino]ethyl 5-(2-chloro-4-trifluoromethylphenoxy)-2-nitrobenzoate was identified as follows; nmr (CDCl$_3$) δ3.3–4.0 (m, 6H), 4.35 (t, 2H), 4.77–6.28 (m, 7H), 6.80–8.22 (m, 6H); ir (CHCl$_3$) 1750 Cm$^{-1}$.

TABLE II

Herbicidal Effectiveness of Post-Emergence Application (At 10 lbs./acre)

| Ex. No. | MNGY | MSTD | FOX | JPN | CRB | PIG |
|---|---|---|---|---|---|---|
| 1 | 9 | 9 | 9 | 9 | 9 | 9 |
| 2 | 9 | 9 | 9 | 8 | 9 | 9 |
| 3 | 6 | 9 | 9 | 8 | 9 | 9 |
| 4 | 9 | 9 | 9 | 5 | 7 | 9 |
| 5 | 8 | 9 | 8 | 4 | 5 | 9 |
| 6 | 5 | 6 | 8 | 5 | 9 | 9 |
| 7 | 8 | 8 | 7 | 0 | 6 | 9 |

*Rated on scale of 0 to 9, from no visible effect on foliage to 100% destruction; with MNGY = morning glory, MSTD = mustard, FOX = yellow foxtail, JPN = Japanese millet, CRB = crabgrass, PIG = pigweed.

TABLE III

Herbicidal Effectiveness of Pre-Emergence Application (At 10 lbs./acre)

| Ex. No. | MNGY | MSTD | FOX | JPN | CRB | PIG |
|---|---|---|---|---|---|---|
| 1 | 9 | 9 | 9 | 9 | 9 | 9 |
| 2 | 9 | 9 | 9 | 9 | 9 | 9 |
| 3 | 9 | 9 | 9 | 9 | 9 | 9 |
| 4 | 5 | 9 | 8 | 6 | 9 | 9 |
| 5 | 9 | 9 | 6 | 8 | 9 | 9 |
| 6 | 9 | 9 | 9 | 9 | 9 | 9 |
| 7 | 9 | 9 | 9 | 9 | 9 | 9 |

*Rated on scale of 0 to 9, from no visible effect on foliage to 100% destruction; with MNGY = morning glory, MSTD = mustard, FOX = yellow foxtail, JPN = Japanese millet, CRB = crabgrass, PIG = pigweed.

TABLE IV

| | CROP SELECTIVITY | |
|---|---|---|
| | Compound* of Ex. 1 | Comparative* Example (BLAZER) |
| Plant tested (Pre Emergence) | | |
| Weeds: MNGY | 9 | 9 |
| MSTD | 9 | 9 |
| FOX | 8 | 7 |
| PIG | 9 | 9 |
| COCL (1) | 8 | 7 |
| VEL (2) | 9 | 9 |
| LAM (3) | 9 | 9 |
| Crops: Corn | 0 | 9 |
| Wheat | 0 | 8 |
| Rice | 0 | 7 |
| Plant tested (Post Emergence**) | | |
| Weeds: MNGY | 9 | 8 |
| MSTD | 9 | 9 |
| FOX | 7 | 9 |
| PIG | 9 | 9 |
| COCL (1) | 9 | 9 |
| VEL (2) | 9 | 9 |
| LAM (3) | 9 | 9 |
| Crops: Corn | 4 | 9 |
| Wheat | 5 | 9 |
| Rice | 3 | 6 |

*application rate at 2 pounds/acre
**2 week old plants
(1) cocklebur
(2) velvet leaf
(3) lambsquarters In summary, the compounds of this invention show high pre- and post-emergence herbicidal activity against indicated weeds, and are particularly effective against broadleaf weeds, such as morning glory. In addition to such effective herbicidal activity, they exhibit an unusual selectivity against important agromonic crops, such as cotton, rice and soybean.

While the invention has been described with particular reference to certain embodiments thereof, it will be understood that certain modifications and changes may be made which are within the skill of the art. Therefore it is intended to be bound only by the appended claims.

What is claimed is:

1. A method of selectively controlling undesirable plant growth in an area where corn, wheat and rice are grown which comprises applying to said area a weed growth controlling amount of the herbicide 2-(N,N-diethylcarbamyloxy)ethyl-5-(2-chloro-4-trifluoromethylphenoxy)-2-nitrobenzoate.

* * * * *